US009234831B2

United States Patent
Takakura (10) Patent No.: US 9,234,831 B2
(45) Date of Patent: Jan. 12, 2016

(54) PARTICLE ANALYSIS INSTRUMENT AND COMPUTER PROGRAM

(71) Applicant: JEOL Ltd., Tokyo (JP)

(72) Inventor: Masaru Takakura, Tokyo (JP)

(73) Assignee: JEOL Ltd., Tokyo (JP)

( * ) Notice: Subject to any disclaimer, the term of this patent is extended or adjusted under 35 U.S.C. 154(b) by 0 days.

(21) Appl. No.: 14/613,596

(22) Filed: Feb. 4, 2015

(65) Prior Publication Data

US 2015/0219547 A1 Aug. 6, 2015

(30) Foreign Application Priority Data

Feb. 6, 2014 (JP) .................................. 2014-21126

(51) Int. Cl.
*H01J 37/28* (2006.01)
*H01J 37/04* (2006.01)
*G01N 15/14* (2006.01)
*G06K 9/00* (2006.01)

(52) U.S. Cl.
CPC ........ *G01N 15/1434* (2013.01); *G01N 15/1429* (2013.01); *G01N 15/1463* (2013.01); *G06K 9/00* (2013.01); *H01J 37/28* (2013.01); *H01J 2237/2448* (2013.01); *H01J 2237/2813* (2013.01)

(58) Field of Classification Search
CPC ......... H01J 37/28; H01J 37/04; H01J 37/244; H01J 37/265; H01J 37/05; H01J 37/295
USPC ............... 250/307, 310, 311, 305, 306, 492.3
See application file for complete search history.

(56) References Cited

U.S. PATENT DOCUMENTS

| 5,659,174 | A | * | 8/1997 | Kaneoka | ............... | H01J 37/256 250/307 |
| 7,202,476 | B2 | * | 4/2007 | Suga | .................... | G01N 23/225 250/310 |
| 7,745,785 | B2 | * | 6/2010 | Nishiyama | ........... | G01N 23/225 250/306 |
| 7,791,022 | B2 | * | 9/2010 | Nakamura | ............. | G01B 15/00 250/306 |
| 8,772,714 | B2 | * | 7/2014 | Yamazaki | ............... | H01J 37/26 250/311 |
| 8,785,850 | B2 | * | 7/2014 | Malac | ..................... | H01J 37/04 250/311 |
| 2001/0035495 | A1 | * | 11/2001 | Nagai | ..................... | H01J 37/28 250/311 |
| 2009/0114817 | A1 | * | 5/2009 | Bullock | ............. | G01R 31/2831 250/307 |
| 2015/0014527 | A1 | * | 1/2015 | Otsuka | ................... | H01J 37/244 250/307 |
| 2015/0213995 | A1 | * | 7/2015 | Muray | .................... | H01J 37/04 250/305 |

(Continued)

FOREIGN PATENT DOCUMENTS

JP 2000214112 A 8/2000

*Primary Examiner* — David A Vanore
(74) *Attorney, Agent, or Firm* — The Webb Law Firm (57) ABSTRACT

A particle analysis instrument is offered which can make a measurement in a shorter time than heretofore. The particle analysis instrument (100) is used to analyze a sample (S) containing plural particles by measuring the sample over plural fields of view. The instrument (100) includes a measuring section (10) for scanning primary rays (EB) over the sample (S) and detecting a signal emanating from the sample (S), a particle area totalizing portion (222) for finding the area of particles for each field of view from the results of the measurement made by the measuring section (10) and summing up such areas of particles for all of the fields of view to find a total area of particles, and a decision portion (226) for making a decision as to whether the measurement process should be ended, based on the ratio of the total area of particles to an area of the sample (S) measured to obtain the total area of particles.

8 Claims, 4 Drawing Sheets

(56) References Cited

U.S. PATENT DOCUMENTS

2015/0219547 A1* 8/2015 Takakura ........... G01N 15/1434
250/307

2015/0235833 A1* 8/2015 Bazargan .............. H01J 49/105
702/189

* cited by examiner

PARTICLE ANALYSIS INSTRUMENT AND COMPUTER PROGRAM

BACKGROUND OF THE INVENTION

1. Field of the Invention

The present invention relates to a particle analysis instrument and a computer program.

2. Description of Related Art

Automated particle analysis methods using a scanning electron microscope, an electron probe microanalyzer, or the like are known (see, for example, JP-A-2000-214112). In such an instrument, a backscattered electron image indicating a chemical composition or a secondary electron image, for example, is obtained. Particles are extracted using a contrast threshold value previously set using a reference sample. Characteristic X-rays are measured by an energy-dispersive detector or a wavelength-dispersive detector. The particles are classified using the intensity values of the measured characteristic X-rays or concentration values. This measurement is repeated for the full range of a previously set field of view, for all of a previously set number of fields of view, or for all of a previously set number of particles.

The purposes of material analysis by automated particle analysis using a scanning electron microscope or electron probe microanalyzer are roughly classified into two major categories: one is to find the average composition of a material; the other is to extract trace components from the sample. The average composition of a sample can be found, for example, by calculating the ratio of the area of particles to the total measured area of the sample.

In the above-described automated particle analysis method, the measurement is repeated for the full range of a previously set field of view, for all of a previously set number of fields of view, or for all of a previously set number of particles. At this time, there are no problems concerning the purpose of extracting trace components from the sample.

However, where the average composition of a sample should be identified, even if the ratio of the total area of extracted particles to the total area of fields of view used for analysis settles down to a constant value with the used fields of view being much smaller in number than the set fields of view, it is not possible that the present measurement is ended and the process shifts to a measurement of another analysis sample unless the measurement in the remaining fields of view is complete. Accordingly, the total analysis time may be quite long.

SUMMARY OF THE INVENTION

In view of the foregoing problems, the present invention has been made. One object associated with some aspects of the present invention is to provide a particle analysis instrument and computer program capable of performing a measurement in a shorter time than heretofore.

(1) A particle analysis instrument associated with the present invention is adapted to analyze a sample containing a plurality of particles by measuring the sample across a plurality of fields of view. The particle analysis instrument includes: a measuring section for scanning primary rays over the sample and detecting a signal emanating from the sample; a particle area totalizing portion for finding a particle area for each of the fields of view from results of measurements performed by the measuring section and summing up such particle areas for all of the fields of view to find a total area of particles; and a decision portion for making a decision as to whether the measurement process should be ended, based on the ratio of the total area of particles to an area of the sample measured to obtain the total area of particles.

In this particle analysis instrument, a measurement for obtaining information about the average composition of the sample (i.e., the ratio of the total particle area to the measured area of the sample) can be performed in a shorter time than heretofore.

(2) In one feature of this particle analysis instrument, the decision portion may determine that the measurement process should be ended if the value of $|C(n)-C(n-1)|$ is smaller than a given value, where n is the number of fields of view and $C(n)$ is the ratio of the total area of particles to the measured area of the sample in a case where the number of fields of view is n.

In this particle analysis instrument, a measurement for obtaining information about the average composition of the sample can be performed in a shorter time than heretofore.

(3) In another feature of this particle analysis instrument, the measuring section performs elemental analysis of the particles. The particle area totalizing portion classifies the particles, based on results of the elemental analysis and finds the total area of particles for each type of the classified particles. The decision portion may perform a decision as to whether the measurement process should be ended, based on the ratio of the total area of particles to the measured area of the sample for each type of the classified particles.

This particle analysis instrument can obtain information about an average composition of a sample containing plural particles which are different in composition.

(4) In a further feature of this particle analysis instrument, the decision portion may make a decision as to whether the value of $|C(n)-C(n-1)|$ (where n is the number of fields of view and $C(n)$ is the ratio of the total area of particles to the measured area of the sample in a case where the number of fields of view is n) is smaller than the given value for each type of the classified particles and determine that the measurement process should be ended if the value of $|C(n)-C(n)-1)|$ is smaller than the given value for all the types of the classified particles.

This particle analysis instrument can obtain information about an average composition of a sample containing plural particles which are different in composition.

(5) A computer program associated with the present invention operates to analyze a sample containing a plurality of particles by measuring the sample across a plurality of fields of view. The program has computer code for causing a computer to operate: as a controller for controlling a measuring section of a particle analysis instrument such that primary rays are scanned over the sample and that a signal emanating from the sample is detected; as a particle area totalizing portion for finding a particle area for each of the fields of view from results of measurements performed by the measuring section and summing up such particle areas for all of the fields of view to find a total area of particles; and as a decision portion for making a decision as to whether the measurement process should be ended, based on the ratio of the total area of particles to an area of the sample measured to obtain the total area of particles.

This computer program permits a measurement for obtaining information about the average composition of the sample to be performed in a shorter time than heretofore.

(6) In one feature of this computer program, the decision portion may determine that the measurement process should be ended if the value of $|C(n)-C(n-1)|$ is smaller than a given value, where n is the number of fields of view and $C(n)$ is the ratio of the total area of particles to the measured area of the sample in a case where the number of fields of view is n.

This computer program permits a measurement for obtaining information about the average composition of the sample to be performed in a shorter time than heretofore.

(7) In another feature of this computer program, the controller may control the measuring section such that elemental analysis of the particles is performed. The particle area totalizing portion may classify the particles, based on results of the elemental analysis and find the total area of particles for each type of the classified particles. The decision portion may make a decision as to whether the measurement process should be ended, based on the ratio of the total area of particles to the measured area of the sample for each type of the classified particles.

This computer program makes it possible to obtain information about an average composition of a sample containing a plurality of particles which are different in composition.

(8) In a further feature of this computer program, the decision portion may make a decision as to whether the value of $|C(n)-C(n-1)|$ is smaller than a given value, where n is the number of fields of view and C(n) is the ratio of the total area of particles to the measured area of the sample in a case where the number of fields of view is n, for each type of the classified particles, and determine that the measurement process should be ended if the value of $|C(n)-C(n-1)|$ is smaller than the given value for all of the types of the classified particles.

This computer program makes it possible to obtain information about an average composition of a sample containing a plurality of particles which are different in composition.

DESCRIPTION OF THE INVENTION

The preferred embodiments of the present invention are hereinafter described in detail with reference to the accompanying drawings. It is to be noted that embodiments described below do not unduly restrict the scope of the invention delineated by the appended claims and that not all the configurations set forth below are essential components of the invention.

1. Particle Analysis Instrument

Figure 1:
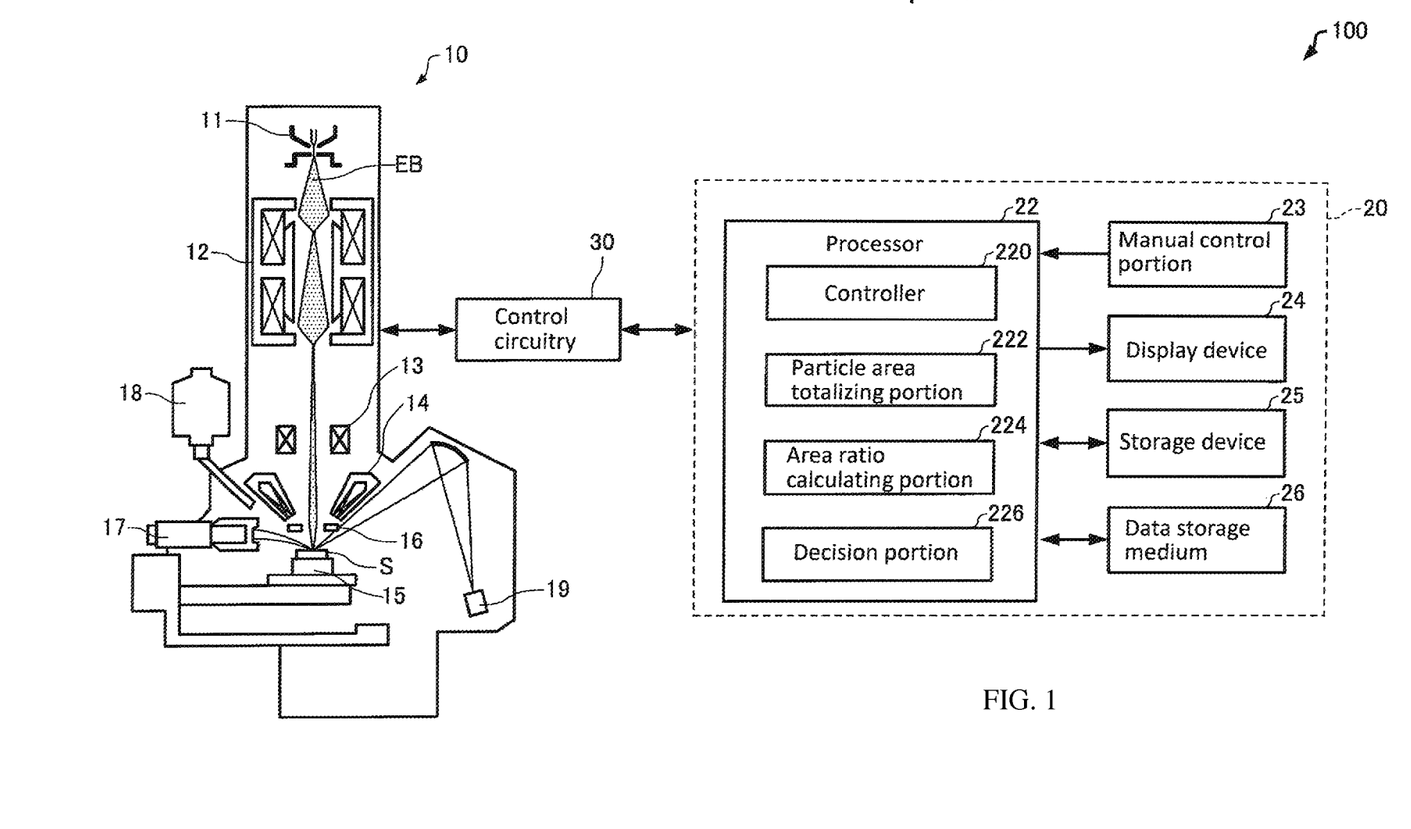
FIG. 1 is a schematic view of a particle analysis instrument associated with one embodiment of the present invention.

A particle analysis instrument associated with one embodiment of the present invention is first described by referring to FIG. 1, in which the instrument is generally indicated by reference numeral 100.

The particle analysis instrument 100 has a function of automated particle analysis. That is, this instrument is made of a scanning electron microscope (SEM) or an electron probe microanalyzer (EPMA) and can obtain an electron beam image by scanning the surface of a sample with a sharply focused electron beam. This function is capable of automatically detecting particles on the surface of the sample from information about the obtained electron beam image in accordance with prescribed rules, calculating information about the shape of each particle such as size, deriving information about the composition of each particle by measuring a signal obtained by irradiating each such particle with an electron beam, and classifying the particles in accordance with given rules based on these kinds of information.

The particles referred to herein are particulate tissues locally embedded in a matrix, and are inclusions or deposits, for example, within a sample (such as a steel material).

The particle analysis instrument 100 finds an average composition of a sample S containing a plurality of particles by measuring the sample S across a plurality of fields of view. The average composition of the sample S can be found from the ratio of the area of extracted particles to the area of the sample S used for the measurement. Furthermore, the particle analysis instrument 100 classifies the particles contained in the sample S, finds the ratio of the area of particles to the measured area of the sample S for each particle type of the classified particles, and finds the average composition of the sample S.

As shown in FIG. 1, the particle analysis instrument 100 is configured including a measuring section 10, a personal computer 20, and control circuitry 30.

The measuring section 10 scans primary rays (such as an electron beam EB) over the sample S and detects a signal (such as backscattered electrons, secondary electrons, or characteristic X-rays) emanating from the sample S. The measuring section 10 is configured including an electron gun 11, condenser lenses 12, a deflector 13, an objective lens 14, a sample stage 15, a backscattered electron detector 16, a secondary electron detector 17, an energy-dispersive detector 18, and a wavelength-dispersive detector 19. It is herein assumed that the measuring section 10 is an electron probe microanalyzer (EPMA).

The electron gun 11 produces the electron beam EB, which is accelerated by a given accelerating voltage, toward the sample S.

The condenser lenses 12 are located behind the electron gun 11 (on the downstream side of the electron gun 11 as viewed along the electron beam EB). The condenser lenses 12 are used to focus the beam EB.

The deflector 13 is located behind the condenser lenses 12 and can deflect the electron beam EB. Since a scan signal is applied to the deflector 13 via the control circuitry 30, the electron beam EB focused by the condenser lenses 12 and objective lens 14 can be scanned over the sample S.

The objective lens 14 is located behind the deflector 13. The objective lens 14 is used such that the electron beam EB is focused onto the sample S and that the beam EB is directed as an electron probe at the sample S.

The sample stage 15 can support the sample S thereon. That is, the sample S is placed on the sample stage 15. The sample stage 15 is moved by operation of a stage drive mechanism (not shown) having a drive source such a motor under control of a controller 220. The location of analysis on the sample S irradiated with the electron beam EB (electron probe) can be moved in a relative manner by movement of the sample stage 15.

The backscattered electron detector 16 is used to detect backscattered electrons which are reemitted from the surface of the sample in a process where incident electrons scatter within the sample S. For example, the backscattered electron detector 16 is an annular detector. A backscattered electron image can be created from the output signal from the backscattered electron detector 16. The output signal from the backscattered electron detector 16 is stored as image data synchronized with the scan signal for the electron beam EB, for example, in a storage device 25.

A BSE (backscattered secondary electron) compositional image can be obtained by detecting backscattered electrons by the backscattered electron detector 16. For example, the detector 16 has two detector elements arranged symmetrically with respect to an optical axis. Backscattered electrons are detected by the two detector elements. The outputs from these detector elements are summed up to create an SEM image. Consequently, topographic information is canceled out, and a BSE compositional image having only compositional information can be generated.

The secondary electron detector 17 is used to detect secondary electrons emitted from the sample S. When incident electrons undergo inelastic scattering, electrons inside a solid are excited, thus giving off secondary electrons into a vacuum. For example, the secondary electron detector 17 is an Everhart-Thornley detector. A secondary electron image can be obtained from the output signal from the secondary electron detector 17. The output signal from the secondary electron detector 17 is stored as image data synchronized with the scan signal for the electron beam EB, for example, in the storage device 25.

The energy-dispersive detector 18 is an energy-dispersive X-ray detector used to discriminate X-rays according to their energy and to obtain a spectrum. The energy-dispersive detector 18 detects characteristic X-rays produced when the sample S is irradiated with the electron beam EB.

The wavelength-dispersive detector 19 separates certain wavelengths of X-rays by making use of Bragg reflections of X-ray from an analyzing crystal and detects the wavelengths. The detector 19 separates and detects characteristic X-rays produced when the sample S is irradiated with the electron beam EB.

The personal computer 20 is configured including a processor 22, a manual control portion 23, a display device 24, the aforementioned storage device 25, and a data storage medium 26.

The manual control portion 23 obtains a manual control signal responsive to a user's action or manipulation and sends the signal to the processor 22. For example, the manual control portion 23 is made of buttons, keys, a touch panel display, or a microphone.

The display device 24 displays images generated by the processor 22. The function of the display device 24 can be implemented by an LCD, a CRT, or the like. The display device 24 displays information about an average composition of the sample S calculated by the processor 22. Furthermore, the display device 24 displays a screen (such as a GUI shown in FIG. 2) permitting a user to control the particle analysis instrument 100. In addition, the display device 24 displays a backscattered electron (BSE) compositional image, a secondary electron image, or other image.

The storage device 25 operates as a working area for the processor 22. The function of the storage device 25 can be implemented by a RAM or the like. Programs, data, and other information permitting the processor 22 to perform various types of computational processing and control operations are stored in the storage device 25. Furthermore, the storage device 25 is used to temporarily store the results of calculations carried out by the processor 22 in accordance with various programs.

The data storage medium 26 that is a computer-readable medium stores computer programs, data, and related information. The function of the storage medium 26 can be implemented by an optical disc (such as a CD or a DVD), a magnetooptical disc (MO), a magnetic disc, a hard disc, magnetic tape, a computer memory (such as a ROM), or the like. The processor 22 performs various kinds of processing of the present embodiment in accordance with computer programs and data stored on the data storage medium 26. Computer programs for causing a computer to operate as various parts of the processor 22 can be stored on the storage medium 26. Such programs can be delivered to the storage medium 26 (storage device 25) via a network from a data storage device possessed by a host device (server).

The processor 22 performs various kinds of computational processing in accordance with computer programs stored in the storage device 25. The processor 22 acts as the controller 220, a particle area totalizing portion 222, an area ratio calculating portion 224, and a decision portion 226 described below by executing programs stored in the storage device 25. The function of the processor 22 can be implemented by hardware (such as various processors, e.g., a CPU or a DSP, or an ASIC, e.g., a gate array) or software. At least a part of the processor 22 may be made of hardware (dedicated circuitry).

The controller 220 controls the measuring section 10 via the control circuitry 30 such that the electron beam EB is scanned over the sample S and that a signal emanating from the sample S is detected.

For example, the controller 220 applies a scan signal to the deflector 13 via the control circuitry 30. As a result, a given region on the sample S is scanned by the electron beam EB focused by the condenser lenses 12 and objective lens 14. Consequently, backscattered electrons are generated from the sample S and a backscattered electron signal is obtained from the output signal from the backscattered electron detector 16. Furthermore, secondary electrons are emitted from the sample S and a secondary electron image is obtained from the output signal from the secondary electron detector 17.

Furthermore, the controller 220 controls the measuring section 10 to perform elemental analysis of particles. The controller 220 identifies the position (coordinates) of each particle, for example, from a backscattered electron image or a secondary electron image and emits the electron beam EB. Consequently, elemental analysis of each particle producing characteristic X-rays can be performed by detecting the characteristic X-rays with at least one of the energy-dispersive detector 18 and the wavelength-dispersive detector 19.

The controller 220 controls the measuring section 10 such that the above-described measurement process (i.e., acquisition of a backscattered electron image, acquisition of a secondary electron image, and elemental analysis of particles using the detectors 18 and 19) is performed across plural fields of view until the decision portion 226 determines that the measurement process should be ended.

The particle area totalizing portion 222 finds a particle area from the results of a measurement by the measuring section 10 for each field of view and finds the total area of the particles by summing up such particle areas for all of the fields of view.

The particle area totalizing portion 222 finds the area of particles for each field of view, for example, from contrast information obtained by making a measurement using the backscattered electron detector 16. The area of the particles is found by counting the number of pixels contained in a region regarded as being occupied by particles, for example, in a BSE compositional image. The totalizing portion 222 finds the total area of the particles by summing up the areas of the particles respectively obtained in different fields of view of the BSE compositional image.

Alternatively, the particle area totalizing portion 222 may find the area of particles in each field of view from contrast information (such as a secondary electron image) obtained empirically using the secondary electron detector 17.

Where the sample S contains particles of different elemental compositions, the particle area totalizing portion 222 classifies particles on the basis of the results of the element analysis performed by the measuring section 10 and finds the total area of particles for each type of the classified particles. For example, the particle area totalizing portion 222 classifies particles according to detection intensities or concentrations (composition) of particles, using the results of detections performed by the detectors 18 and 19 or the results of detection performed by the backscattered electron detector 16 (i.e., information about the contrast in a backscattered electron image), and finds the total area of particles for each type of the classified particles.

The area ratio calculating portion 224 calculates the ratio of the total area of particles to the area of the sample S measured to obtain the total area of particles by the particle area totalizing portion 222. The measured area of the sample S can be found, for example, by computing the product of the area of one field of view and the number of fields of view.

The decision portion 226 makes a decision as to whether the measurement process should be ended, based on the ratio of the total area of particles to the area of the sample S measured to obtain the total area of particles. Let n be the number of fields of view. Let $C(n)$ be the ratio of the total area of particles to the measured area of the sample in a case where the number of fields of view is n. If the value of $|C(n)-C(n-1)|$ is smaller than a given threshold value, the decision portion 226 terminates the measurement process. Where the number of fields of view is n, the measured area of the sample is found, for example, by multiplying the number of fields of view, n, by the area of one field of view. Where the number of fields of view is n, the total area of particles is computed by the particle area totalizing portion 222 as described previously.

The threshold value is set to a value to which $C(n)$ can be said to have converged when the $|C(n)-C(n-1)|$ is calculated. That is, the threshold value gives a threshold condition for $C(n)$. A user can set the threshold value at will. For example, the threshold value is 0.0001.

Figure 2:
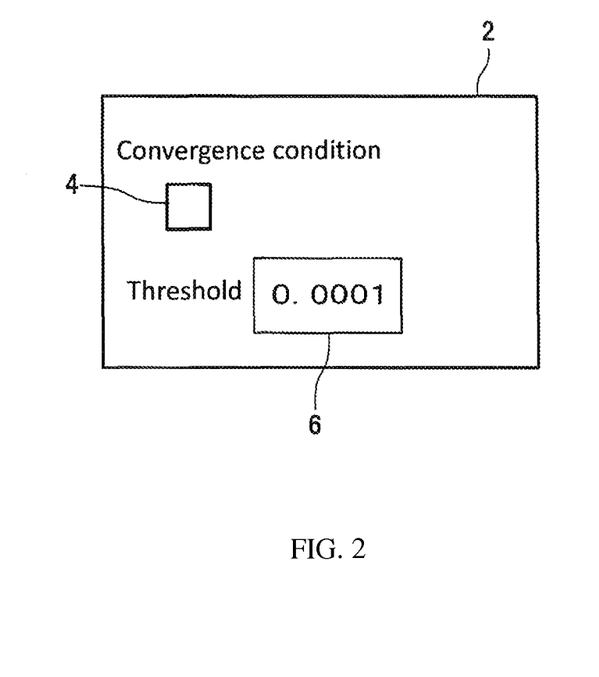
FIG. 2 is a schematic representation of one example of GUI permitting a user to establish a threshold value.
Figure 3:
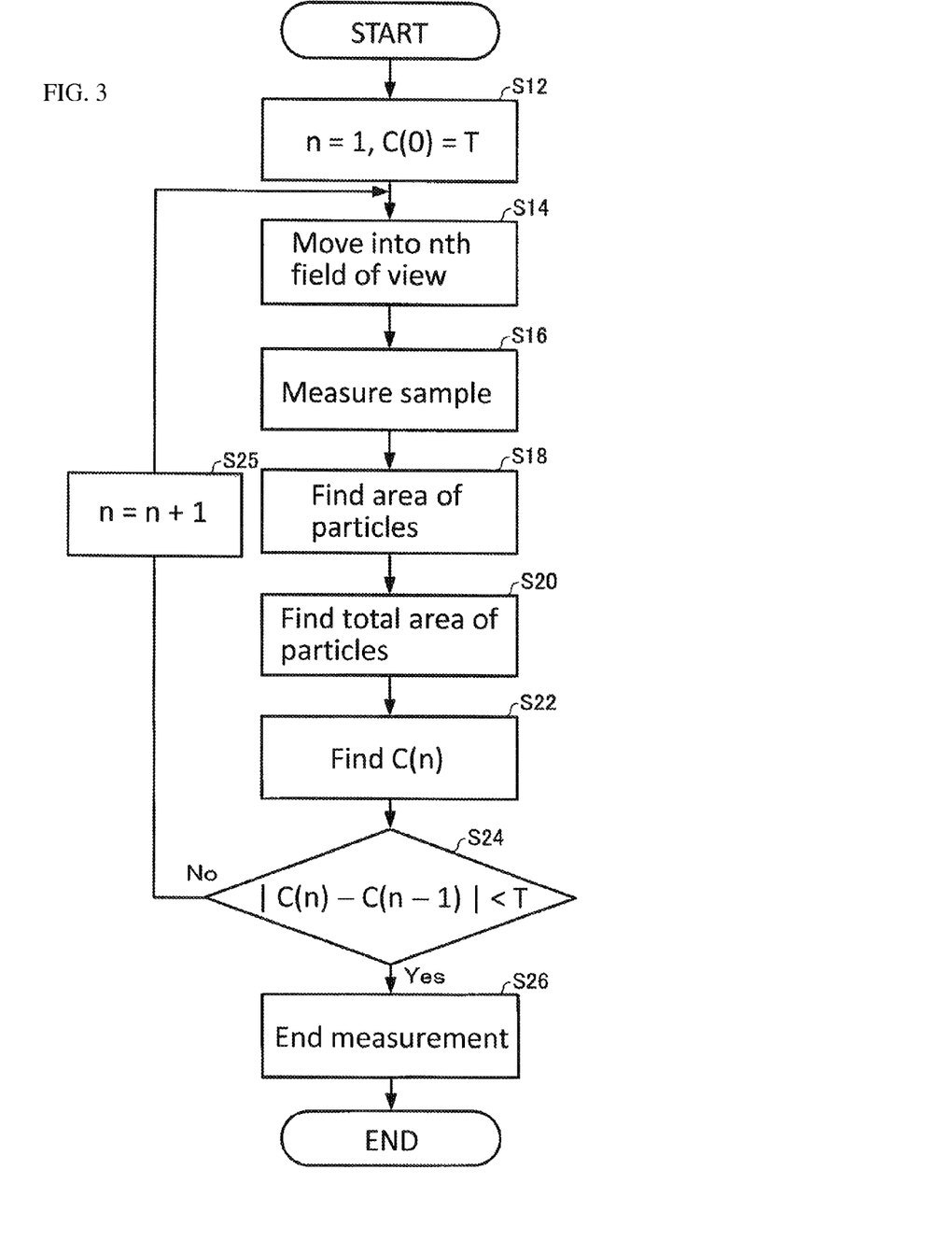
FIG. 3 is a flowchart illustrating one example of subroutine performed by a controller included in the particle analysis instrument shown in FIG. 1.

FIG. 2 schematically shows one example of GUI (graphical user interface), 2, permitting a user to establish the threshold value. A subroutine for calculating an average composition of the sample S as illustrated in FIG. 3 is performed by depressing a button 4 on the GUI 2 shown in FIG. 2. A threshold value can be established by entering a numerical value or values into a threshold input field 6 of the GUI 2.

The decision portion 226 makes a decision as to whether the measurement process should be ended, on the basis of the ratio of the total area of particles of each particle type to the measured area of the sample in a case where the sample S contains particles of different elemental compositions. For example, the decision portion 226 makes a decision as to whether the value of $|C(n)-C(n-1)|$ is smaller than the threshold value for each type of the classified particles, and determines that the measurement process should be ended if the value of $|C(n)-C(n-1)|$ is smaller than the threshold value for all of the types of the classified particles. If the value of $|C(n)-C(n-1)|$ is not smaller than the threshold value for any one type of the classified particles, the decision portion 226 determines that the measurement process is not ended but continued.

2. Operation of Particle Analysis Instrument

Figure 4:
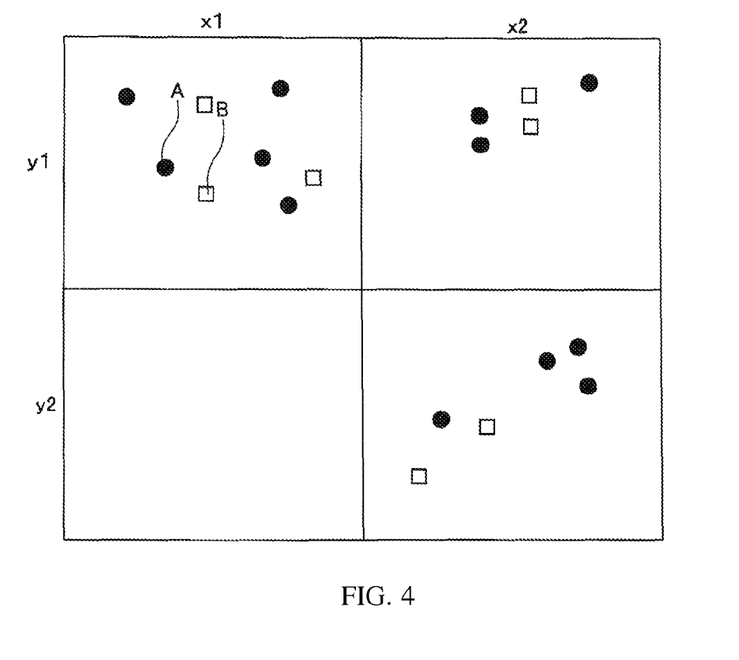
FIG. 4 is a chart illustrating the operation of the particle analysis instrument shown in FIG. 1.

The operation of the particle analysis instrument associated with the present embodiment is next described by referring to FIGS. 3 and 4. FIG. 3 is a flowchart illustrating one example of subroutine performed by the processor 22 of the particle analysis instrument 100. FIG. 4 illustrates the operation of the particle analysis instrument 100, depicting fields of view on the measured sample S. Coordinates (x, y) shown in FIG. 4 indicate the positions of the fields of view.

First, the processor 22 sets conditions, n=1 and C(0)=T (where T is a threshold value) (step S12).

Then, the controller 220 controls the sample stage 15 to move the sample stage 15 into the nth field of view (step S14). For example, where n=1, the controller 220 controls the sample stage 15 to bring the stage 15 into the field of view indicated by coordinates (x1, y1) shown in FIG. 4.

The controller 220 controls the measuring section 10 to perform a measurement on the sample S in the nth field of view (step S16).

In particular, the controller 220 controls the deflector 13 to scan the electron beam EB over the sample S. Backscattered electrons produced from the sample S in response to the irradiation by the electron beam EB are detected by the backscattered electron detector 16. Consequently, information about a BSE compositional image in the nth field of view is stored in the storage device 25.

Then, the controller 220 extracts particles from the BSE compositional image and performs elemental analysis of each extracted particle. Specifically, the controller 220 first extracts information about the coordinates, number, and diameters of particles which are different in contrast from the matrix in which particles are embedded from the contrast information contained in the BSE compositional image. The controller 220 then controls the deflector 13 on the basis of information about each extracted particle, and directs the electron beam EB, for example, at the center of gravity of the particle. Characteristic X-rays produced from the particle in response to the irradiation are detected by the energy-dispersive detector 18 and the wavelength-dispersive detector 19. The output signals from the detectors 18 and 19 are stored, for example, in the storage device 25. The controller 220 performs elemental analyses of all of the particles extracted from the nth field of view.

For example, in a case where n=1, the controller 220 extracts particles of types A and B from the backscattered electron image in the field of view indicated by the coordinates (x1, y1) shown in FIG. 4 and extracts information about the coordinates, number, particle diameters, and so on. Although the particle types A and B are different in composition, these are not herein distinguished from each other. The 8 extracted particles, each being of particle type A or B, are each subjected to elemental analysis.

In the above description, particles are extracted using a BSE compositional image. Alternatively, particles may be extracted using a secondary electron image. That is, secondary electrons emanating from the sample S in response to irradiation by the electron beam EB are detected by the secondary electron detector 17 and a secondary electron image is obtained. Particles may be extracted from contrast information contained in the secondary electron image.

Then, the particle area totalizing portion 222 finds the area of the particles in the nth field of view on the basis of the result of the measurement made by the measuring section 10 (step S18).

In particular, the particle area totalizing portion 222 first classifies particles, based on the results of elemental analyses of the particles, for example, by finding an elemental composition of each particle from the results of detections performed by the detectors 18, 19, the results being stored in the storage device 25. Then, the particle area totalizing portion 222 finds the area of the classified particles for each particle type, for example, from the number of extracted particles, the diameters of the particles, or other factor.

For example, in a case where n=1, the particle area totalizing portion 222 classifies particles contained in the field of view indicated by the coordinates (x1, y1) into particle type A and particle type B according to the results of the detections done by the detectors 18 and 19 and finds the area of the particle type A and the area of the particle type B.

Then, the particle area totalizing portion 222 totalizes the areas of classified particles of each type (step S20). For example, the particle area totalizing portion 222 finds the total area of the particles of type A contained in the first to nth fields of view. Furthermore, the particle area totalizing portion 222 finds the total area of the particles of type B contained in the first to nth fields of view.

Then, the area ratio calculating portion 224 finds the ratio C(n) of the total area of particles to the measured area of the sample (step S22) for each type of the classified particles. More specifically, the area ratio calculating portion 224 finds the measured area of the sample, using the formula, n (the number of fields of view)×area of one field of view. The total area of the particles of type A found by the particle area totalizing portion 222 is divided by the measured area of the sample. Consequently, the ratio CA(n) of the total area of the particles of type A to the measured area of the sample is found. By performing a similar process, the area ratio calculating portion 224 finds the ratio CB(n) of the total area of the particles of type B to the measured area of the sample.

The decision portion 226 then makes a decision as to whether each particle type satisfies the relationship, $|C(n)-C(n-1)| < T$ (where T is a threshold value), (step S24). For example, where the threshold value T is set to 0.0001, the decision portion 226 makes a decision as to whether the relationship, $|CA(n)-CA(n-1)| < 0.0001$, is satisfied. Similarly, the decision portion 226 makes a decision as to whether the relationship, $|CB(n)-CB(n-1)| < 0.0001$, is satisfied.

If the decision at step S24 is No, indicating that any one or both of these two relationships ($|CA(n)-CA(n-1)| < T$ and $|CB(n)-CB(n-1)| < T$) are not satisfied, the processor 22 increments the number n by 1 (n=n+1) (step S25). The controller 220 controls the sample stage 15 to move the stage 15 into the nth field of view set at step S25 (step S14). The sample S is measured (step S16). In this nth field of view, the processor 22 performs steps S18, S20, S22, and S24.

In this way, the processor 22 performs the steps S14, S16, S18, S20, S22, S24, and S25 in the order of the first field of view indicated by coordinates (x1, y1), the second field of view indicated by coordinates (x2, y1), the third field of view indicated by coordinates (x1, y2), and the fourth field of view indicated by coordinates (x2, y2), shown in FIG. 4.

The processor 22 repeats the entire processing sequence of steps S14, S16, S18, S20, S22, S24, and S25 until it is determined that the relationship, $|C(n)-C(n-1)| < T$, is satisfied for all of the types of classified particles. That is, the processor 22 moves the current field of view (step S14) and measures the sample S across a plurality of fields of view (step S16) until it is determined that the relationship, $|C(n)-C(n-1)| < T$, is satisfied for all of the types of the classified particles. The area of particles is found for each field of view and the total area of particles is calculated (steps S18 and S20). The value of C(n) is computed (step S22). A decision as to whether that relationship, $|C(n)-C(n-1)| < T$, is satisfied is made (step S24).

If the decision at step S24 is affirmative (Yes) indicating that the relationship, $|C(n)-C(n-1)| < T$, is satisfied, i.e., both of the relationships $|CA(n)-CA(n-1)| < T$ and $|CB(n)-CB(n-1)| < T$ are satisfied, the controller 220 terminates the measurement process (step S26).

In the present process, the controller 220 may terminate the measurement of the sample S and start to measure a next sample. Furthermore, in the present process, the processor 22 may perform processing for displaying information (CA(n) and CB(n)) about an average composition of the sample S on the display device 24.

The particle analysis instrument 100 has the following features. The particle analysis instrument 100 includes: the measuring section 10 for scanning the electron beam EB over the sample and detecting a signal emanating from the sample S; the particle area totalizing portion 222 for finding the area of particles for each field of view from results of measurements made by the measuring section 10 and summing up such areas of particles for all of the fields of view to find a total area of particles; and the decision portion 226 for making a decision as to whether the measurement process should be ended according to the ratio of the total area of particles to the area of the sample S measured to obtain the total area of particles. Consequently, the time taken to perform measurements for obtaining information about an average composition (information about C(n)) of the sample S can be shortened.

In the particle analysis instrument 100, let n be the number of fields of view and C(n) be the ratio of the total area of particles to the measured area of the sample S in a case where the number of fields of view is n. If the value of $|C(n)-C(n-1)|$ is smaller than the threshold value, the decision portion 226 determines that the measurement process should be ended. Therefore, the time taken to perform a measurement for obtaining information about an average composition (information about C(n)) of the sample S can be shortened.

In the particle analysis instrument 100, the measuring section 10 performs elemental analysis of particles. The particle area totalizing portion 222 classifies particles, based on the results of the elemental analysis and fords a total area of particles for each particle type. The decision portion 226 makes a decision as to whether the measurement process should be ended, based on the ratio of the total area of particles to the measured area of the sample for each particle type. Consequently, information about an average composition of a sample containing a plurality of particles which are different in composition can be obtained.

In the particle analysis instrument 100, let n be the number of fields of view and C(n) be the ratio of the total area of particles to the area of a sample used for the measurement in a case where the number of fields of view is n. The decision portion 226 makes a decision as to whether the value of $|C(n)-C(n-1)|$ is smaller than a threshold value for each particle type of the classified particles and determines that the measurement process should be ended if the decision is affirmative for all of the particle types. Therefore, it is possible to obtain information about an average composition of a sample containing plural particles which are different in composition.

A computer program associated with the present embodiment has program code for causing a computer to operate as the controller 220 for controlling the measuring section 10 to scan primary rays over the sample S and to detect a signal emanating from the sample S, as the particle area totalizing portion 222 for finding the area of particles for each field of view from results of measurements made by the measuring section 10 and summing up such areas of particles for all of the fields of view to find the total area of particles; and the decision portion 226 for making a decision as to whether the present measurement process should be ended, based on the ratio of the total area of particles to the area of the sample used for the measurements to obtain the total area of particles. Therefore, the time taken to perform the measurements to obtain information about an average composition (information about C(n)) of the sample S can be shortened as described previously.

Figure 5:
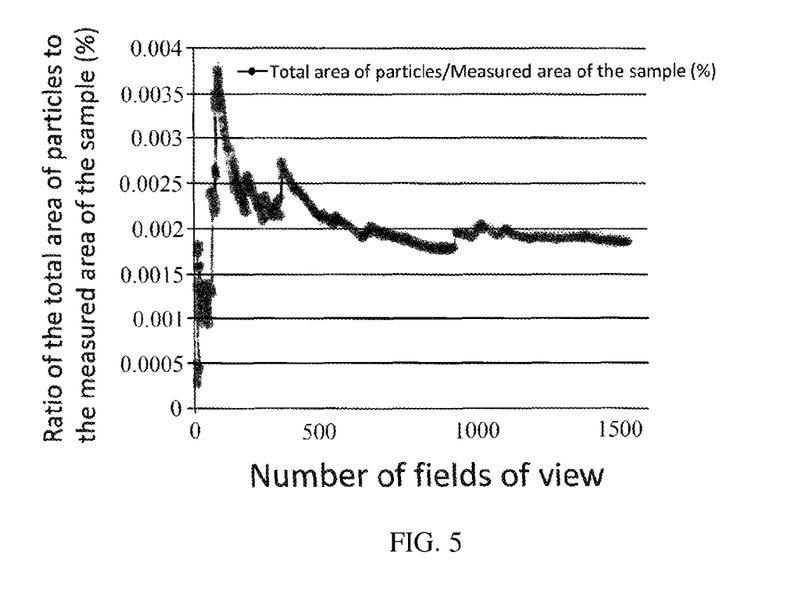
FIG. 5 is a graph showing the results of an automated particle analysis of a sample made of a steel material containing trace amounts of deposits.

FIG. 5 shows the results of an automated particle analysis of a steel material containing trace amounts of deposits. In the graph of FIG. 5, the horizontal axis indicates the number of fields of view used for the particle analysis. The vertical axis indicates the ratio of the total area of particles to the area of the sample used for measurement. The area of each individual particle is measured in terms of the number of pixels contained in regions that are regarded as being occupied by particles when particles are extracted from a BSE (backscattered electron) compositional image. The area of the sample used for measurement is calculated as the area of one field of view established×number of fields of view. In the example of FIG. 5, there are 1530 preset fields of view. Let n be the number of fields of view currently in use. Let n−1 be the number of fields of view used the previous time. Let C(n) be the ratio of the current total area of particles to the area of the sample used for measurement. Let C(n−1) be the ratio of the total area of particles obtained the previous time to the area of the sample used for measurement. If a threshold value used in making a decision as to whether a convergence has been achieved is given by $|C(n)-C(n-1)|<0.0001$, then it follows that the measurement ends with about 500 fields of view. Accordingly, the analysis can be completed in a time that is about one third of the time taken to perform measurements using all of the 1530 set fields of view.

An example in which the measuring section 10 of the particle analysis instrument 100 is an electron probe microanalyzer has been described. The measuring section of the particle analysis instrument associated with the present invention may also be a scanning electron microscope, a scanning transmission electron microscope (STEM), an Auger electron spectroscopy analyzer, or a secondary ion mass analyzer. That is, in the particle analysis instrument associated with the present invention, the primary rays are not restricted to an electron beam. For example, in a secondary ion mass analyzer, ions are used as primary rays.

The present invention embraces configurations substantially identical (e.g., in function, method, and results or in purpose and advantageous effects) with the configurations described in the embodiments of the invention. Furthermore, the invention embraces configurations described in the embodiments and including portions which have non-essential portions replaced. In addition, the invention embraces configurations which produce the same advantageous effects as those produced by the configurations described in the embodiments or which can achieve the same objects as the configurations described in the embodiments. Further, the invention embraces configurations which are similar to the configurations described in the embodiments except that well-known techniques have been added.

Having thus described my invention with the detail and particularity required by the Patent Laws, what is desired protected by Letters Patent is set forth in the following claims.

The invention claimed is:

1. A particle analysis instrument for analyzing a sample containing a plurality of particles by measuring the sample across a plurality of fields of view, said particle analysis instrument comprising:
a measuring section for scanning primary rays over the sample and detecting a signal emanating from the sample;
a particle area totalizing portion for finding a particle area for each of the fields of view from results of measurements performed by the measuring section and summing up such particle areas for all of the fields of view to find a total area of particles; and
a decision portion for making a decision as to whether the measurement process should be ended, based on the ratio of the total area of particles to an area of the sample measured to obtain the total area of particles.

2. The particle analysis instrument as set forth in claim 1, wherein said decision portion determines that the measurement process should be ended if the value of $|C(n)-C(n-1)|$ is smaller than a given value, where n is the number of fields of view and C(n) is the ratio of the total area of particles to the measured area of the sample in a case where the number of fields of view is n.

3. The particle analysis instrument as set forth in claim 1,
wherein said measuring section performs elemental analysis of said particles;
wherein said particle area totalizing portion classifies said particles, based on results of the elemental analysis and finds said total area of particles for each type of the classified particles; and
wherein said decision portion makes a decision as to whether the measurement process should be ended, based on the ratio of the total area of particles to the measured area of the sample for each type of the classified particles.

4. The particle analysis instrument as set forth in claim 3, wherein said decision portion makes a decision as to whether the value of $|C(n)-C(n-1)|$ (where n is the number of fields of view and C(n) is the ratio of the total area of particles to the measured area of the sample in a case where the number of fields of view is n) is smaller than the given value for each type of the classified particles and determines that the measurement process should be ended if the value of $|C(n)-C(n-1)|$ is smaller than the given value for all of the types of the classified particles.

5. A computer program adapted to analyze a sample containing a plurality of particles by measuring the sample across a plurality of fields of view, said computer program having computer code for causing a computer to operate:
as a controller for controlling a measuring section of a particle analysis instrument such that primary rays are scanned over the sample and that a signal emanating from the sample is detected;
as a particle area totalizing portion for finding a particle area for each of the fields of view from results of measurements performed by the measuring section and summing up such particle areas for all of the fields of view to find a total area of particles; and
as a decision portion for making a decision as to whether the measurement process should be ended, based on the ratio of the total area of particles to an area of the sample measured to obtain the total area of particles.

6. The computer program as set forth in claim 5, wherein said decision portion determines that the measurement process should be ended if the value of $|C(n)-C(n-1)|$ is smaller than a given value, where n is the number of fields of view and C(n) is the ratio of the total area of particles to the measured area of the sample in a case where the number of fields of view is n.

7. The computer program as set forth in claim 5,
wherein said controller controls said measuring section such that elemental analysis of said particles is performed;
wherein said particle area totalizing portion classifies said particles, based on results of the elemental analysis and finds said total area of particles for each type of the classified particles; and wherein said decision portion makes a decision as to whether the measurement process should be ended, based on the ratio of the total area of particles to the measured area of the sample for each type of the classified particles.

8. The computer program as set forth in claim 7, wherein said decision portion makes a decision as to whether the value of $|C(n)-C(n-1)|$ is smaller than a given value, where n is the number of fields of view and $C(n)$ is the ratio of the total area of particles to the measured area of the sample in a case where the number of fields of view is n, for each type of the classified particles and determines that the measurement process should be ended if the value of $|C(n)-C(n-1)|$ is smaller than the given value for all of the types of the classified particles.

* * * * *